(12) United States Patent
Wallenstein et al.

(10) Patent No.: US 8,574,272 B2
(45) Date of Patent: Nov. 5, 2013

(54) SEMI-CONSTRAINED SCREW AND SPINAL PLATE ASSEMBLY

(75) Inventors: Todd Wallenstein, Ashburn, VA (US); Larry McClintock, Gore, VA (US); Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 380 days.

(21) Appl. No.: 12/579,162

(22) Filed: Oct. 14, 2009

(65) Prior Publication Data

US 2010/0094357 A1    Apr. 15, 2010

Related U.S. Application Data

(60) Provisional application No. 61/105,067, filed on Oct. 14, 2008.

(51) Int. Cl.
*A61B 17/86* (2006.01)
*A61B 17/80* (2006.01)

(52) U.S. Cl.
USPC ........... 606/291; 606/286; 606/289; 606/305; 606/309

(58) Field of Classification Search
USPC ..................... 606/280–321, 70–71
See application file for complete search history.

(56) References Cited

U.S. PATENT DOCUMENTS

| | | |
|---|---|---|
| 3,054,321 A | 9/1962 | Macchia |
| 5,042,982 A | 8/1991 | Harms et al. |
| 5,057,111 A | 10/1991 | Park |
| 5,085,660 A | 2/1992 | Lin |
| 5,269,784 A | 12/1993 | Mast |
| 5,443,467 A | 8/1995 | Biedermann et al. |
| 5,520,690 A | 5/1996 | Errico et al. |
| 5,531,746 A | 7/1996 | Errico et al. |
| 5,536,127 A | 7/1996 | Pennig |
| 5,591,166 A | 1/1997 | Bernhardt et al. |
| 5,607,426 A | 3/1997 | Ralph et al. |
| 5,607,428 A | 3/1997 | Lin |
| 5,643,265 A | 7/1997 | Errico et al. |
| 5,796,141 A | 8/1998 | Lin et al. |
| 5,876,402 A | 3/1999 | Errico et al. |
| 5,888,204 A | 3/1999 | Ralph et al. |
| 5,904,683 A | 5/1999 | Pohndorf et al. |
| 5,954,722 A | 9/1999 | Bono |
| 6,016,727 A | 1/2000 | Morgan |
| 6,022,350 A | 2/2000 | Ganem |
| 6,129,730 A | 10/2000 | Bono et al. |

(Continued)

OTHER PUBLICATIONS

International Search Report and Written Opinion issued by the U.S. Searching Authority in counterpart PCT Application No. PCT/US2009/060673 mailed Dec. 7, 2009.

*Primary Examiner* — Matthew Lawson
(74) *Attorney, Agent, or Firm* — Carter, DeLuca, Farrell & Schmidt, LLP

(57) ABSTRACT

A semi-constrained screw and a cervical plate assembly that engages to a cervical area of the human vertebrae system are disclosed. The semi-constrained screw and cervical plate assembly includes a cervical plate and one or more semi-constrained bone screws. Each semi-constrained bone screw includes an elongated shank, which is mechanically and releasably coupled to a head portion. The head portion includes one or more threaded segments which define one or more slits therebetween. As the semi-constrained bone screw is driven through the screw opening in the cervical plate and into the bone, the head portion allows poly-axial movement of the shank relative to the head portion.

13 Claims, 8 Drawing Sheets

(56) References Cited

U.S. PATENT DOCUMENTS

| | | |
|---|---|---|
| 6,152,927 A | 11/2000 | Farris et al. |
| 6,206,882 B1 | 3/2001 | Cohen |
| 6,290,703 B1 | 9/2001 | Ganem |
| 6,306,136 B1 | 10/2001 | Baccelli |
| 6,306,140 B1 | 10/2001 | Siddiqui |
| 6,322,562 B1 | 11/2001 | Wolter |
| 6,454,769 B2 | 9/2002 | Wagner et al. |
| 6,595,993 B2 | 7/2003 | Donno et al. |
| 6,602,254 B2 | 8/2003 | Gertzbein et al. |
| 6,656,567 B1 | 12/2003 | Abe et al. |
| 6,663,635 B2 | 12/2003 | Frigg et al. |
| 6,679,883 B2 | 1/2004 | Hawkes et al. |
| 6,716,214 B1 | 4/2004 | Jackson |
| 6,767,351 B2 | 7/2004 | Orbay et al. |
| 6,780,186 B2 | 8/2004 | Errico et al. |
| 6,893,444 B2 | 5/2005 | Orbay |
| 6,936,051 B2 | 8/2005 | Michelson |
| 6,955,677 B2 | 10/2005 | Dahners |
| 6,969,390 B2 | 11/2005 | Michelson |
| 6,979,334 B2 | 12/2005 | Dalton |
| 7,001,389 B1 | 2/2006 | Navarro et al. |
| 7,048,739 B2 | 5/2006 | Konieczynski et al. |
| 7,163,538 B2 | 1/2007 | Altarac et al. |
| 7,175,624 B2 | 2/2007 | Konieczynski et al. |
| 7,229,443 B2 | 6/2007 | Eberlein et al. |
| 7,311,712 B2 | 12/2007 | Dalton |
| 7,318,825 B2 | 1/2008 | Butler et al. |
| 2002/0143338 A1* | 10/2002 | Orbay et al. .......... 606/69 |
| 2005/0137597 A1* | 6/2005 | Butler et al. .......... 606/69 |
| 2006/0041260 A1* | 2/2006 | Orbay .......... 606/69 |
| 2006/0149251 A1* | 7/2006 | Ziolo et al. .......... 606/69 |
| 2006/0200147 A1 | 9/2006 | Ensign et al. |
| 2007/0073298 A1* | 3/2007 | Beutter et al. .......... 606/69 |
| 2008/0215097 A1 | 9/2008 | Ensign et al. |

* cited by examiner

SEMI-CONSTRAINED SCREW AND SPINAL PLATE ASSEMBLY

CROSS-REFERENCE TO RELATED APPLICATIONS

This application claims priority to, and the benefit of, U.S. Provisional Patent Application No. 61/105,067, filed Oct. 14, 2008, the entire contents of which are incorporated herein by reference.

BACKGROUND

1. Technical Field

The present disclosure relates to a spinal plate assembly and, more particularly, to a semi-constrained screw and spinal plate assembly.

2. Background of Related Art

The human spinal column is a highly complex structure. It includes more than twenty discrete bones, known as vertebrae, coupled sequentially to one another to house and protect critical elements of the nervous system. The cervical portion of the spine, which comprises the top of the spine up to the base of the skull, includes the first seven vertebrae.

For many reasons, such as aging and trauma, the intervertebral discs may begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. However, should the prosthetic protrude from the adjacent vertebrae and thereby contact the surrounding nerves or tissues, the patient may experience additional discomfort. In procedures for remedying this problem, a spinal plate assembly having one or more apertures and one or more bone screws is affixed to the vertebrae and oriented to inhibit such protrusion.

A common problem associated with the use of such a spinal plate assembly is the tendency of the bone screws to "back out" or pull away or otherwise withdraw from the bone into which they are mounted. This problem occurs, primarily, due to the normal torsional and bending motions of the body and spine. As the screws become loose and pull away or withdraw from the bone, the heads of the screws can rise above the surface of the plate assembly, which results is pain and discomfort for the patient or possibly the separation of the spinal plate from one or more vertebrae.

SUMMARY

A bone plate assembly for attachment to the vertebrae of the spinal column including a bone plate and one or more semi-constrained screw assemblies are disclosed. The bone plate has at least one opening. The semi-constrained screw assembly includes a removable screw head and a screw shank. The removable screw head and the screw shank each define a longitudinal axis. The removable screw head has a plurality of thread segments, which include one or more slits along at least a portion of the length thereof The screw shank has a proximal end and a distal end. The proximal end is configured to operably couple to the removable screw head. Further, the distal end is configured to operably couple to a bone structure. The semi-constrained screw assembly is configured to be operably coupled into the opening of the bone plate, such that the removable screw head locks to the bone plate, while the screw shank is movable about the longitudinal axis of the removable screw head.

BRIEF DESCRIPTION OF THE DRAWINGS

Embodiments of the presently disclosed spinal plate and screw assembly are described herein with reference to the accompanying drawings, wherein.

DETAILED DESCRIPTION

Figure 1A:
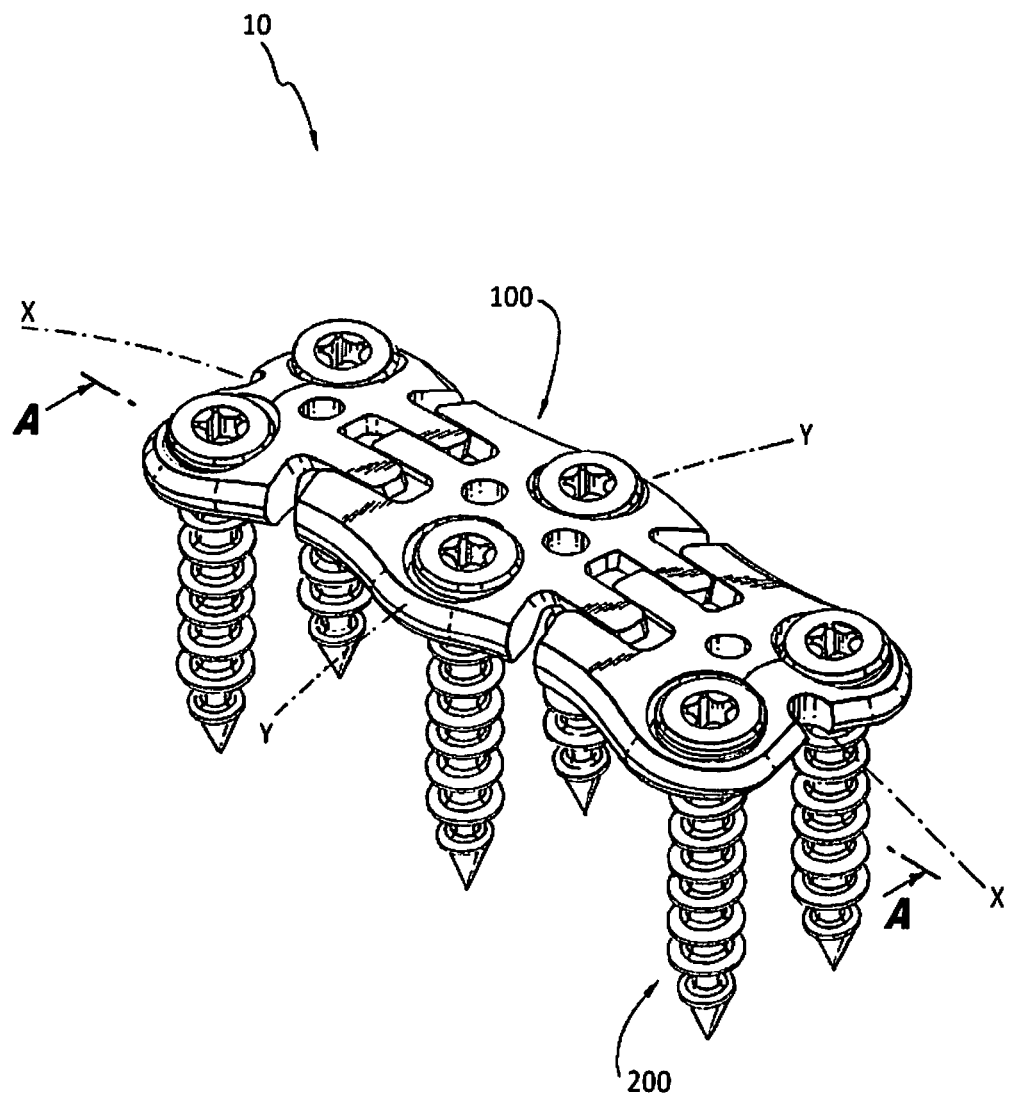
FIG. 1A is a perspective view of a cervical plate system according to an embodiment of the present disclosure having a semi-constrained screw assembly mounted therethrough.
Figure 1B:
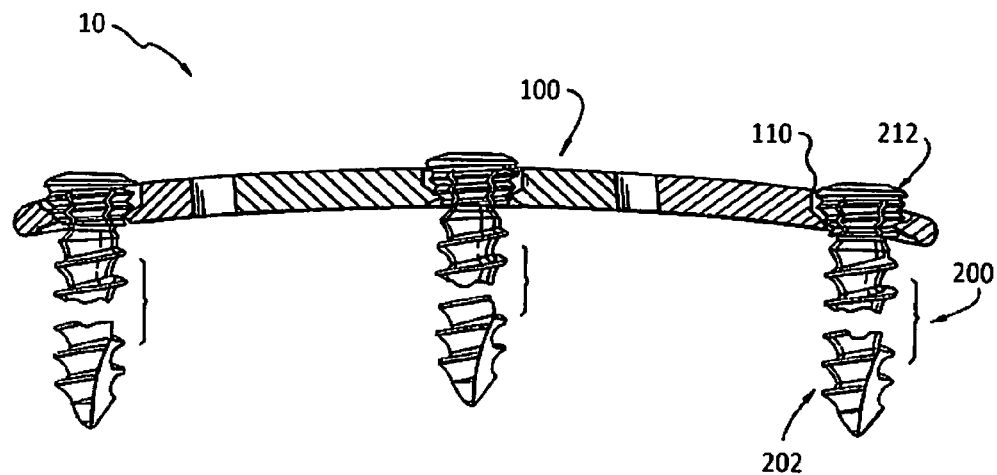
FIG. 1B is a side cross-sectional view, taken along section line A-A, of the cervical plate system of FIG. 1A.
Figure 1C:
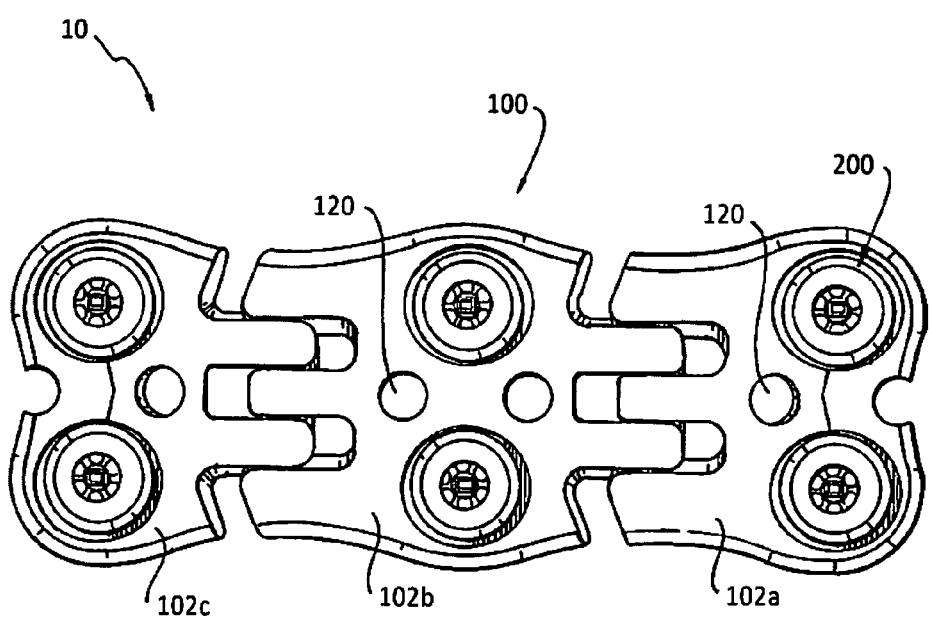
FIG. 1C is a top plan view of the cervical plate system of FIG. 1A.

Various embodiments of the presently disclosed semi-constrained screw and cervical plate assembly will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Referring initially to FIGS. 1A-1D, a semi-constrained screw and cervical plate assembly 10 for engagement to a cervical area of the human vertebrae system is shown according to the present disclosure. The semi-constrained screw and cervical plate assembly 10 includes a cervical plate 100 and one or more semi-constrained bone screws 200. The cervical plate 100 and the semi-constrained bone screws 200 will be discussed in detail below.

Figure 1D:
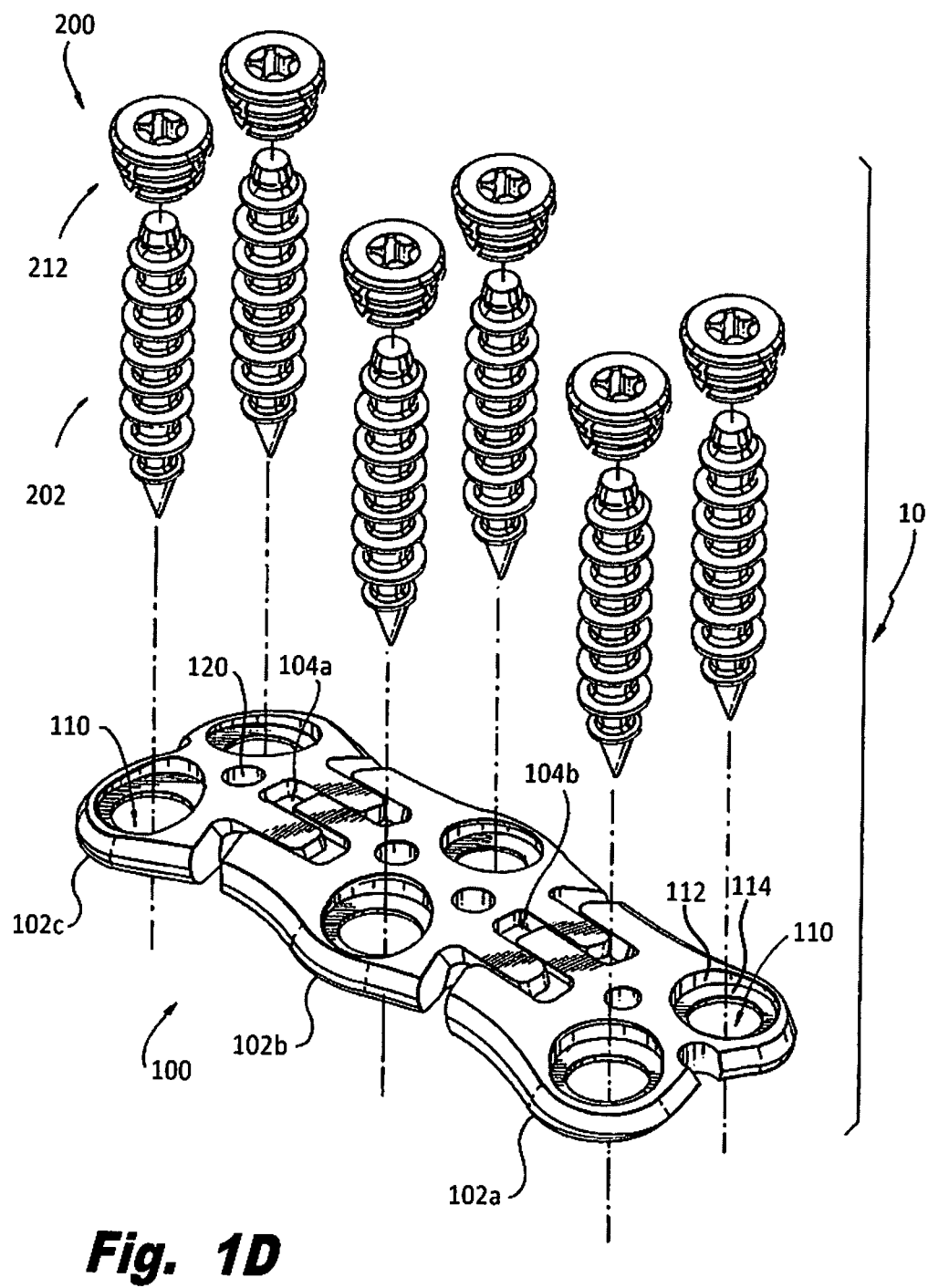
FIG. 1D is an exploded perspective view, with parts separated, of the cervical plate system of FIG. 1A.

Referring now to FIG. 1D, cervical plate 100 is shown having a first end section 102a, a middle section 102b, and a second section 102c. Cervical plate 100 is shown in an extended state, wherein gaps 104a, 104b are defined between the adjacent plate sections 102a, 102b, and 102c. The cervical plate 100 may also be adjusted to be in a collapsed state (not shown), such that plate sections 102a, 102b, and 102c are substantially close together and gaps 104a and 104b are substantially closed.

Each of plate sections 102a, 102b, and 102c of the cervical plate 100 may be manufactured from commercially pure titanium. In addition, cervical plate 100 may be available in different configurations (e.g., size, type of metal used, etc.) and may be anodized into different colors (e.g., green, blue, purple, etc.) to indicate the specific configuration of the plate member to the user.

As shown in FIG. 1A, each of plate sections 102a, 102b, and 102c have a radius of curvature along its longitudinal axis and a radius of curvature (e.g., 1.5 inches) along its lateral axis such that the cervical plate 100 as a whole conforms to adjacent vertebral bodies of a patient's spine.

The cervical plate 100 has a top surface and a bottom surface defining the thickness of the cervical plate 100. In addition, cervical plate 100 includes a plurality of screw openings 110 and one or more guide openings 120, wherein the screw openings 110 and one or more guide openings 120 extend through the thickness of the cervical plate 100. The one or more guide openings 120 are positioned along the central longitudinal axis of the cervical plate 100. Each of the screw openings 110 has an annular sidewall 112 extending downwards from the top surface of the cervical plate 100. A lip 114 is located in each screw opening 110 in proximity to the bottom surface of the cervical plate assembly 100. The lip 114 is configured for engaging a semi-constrained screw 200, 300 (FIGS. 2A and 3A) such that rotating the screw 200, 300 causes the threads of an independent locking head 212, 312 of the respective screw 200, 300 to engage the lip 114. The independent locking head 212, 312 includes threads thereon such that each screw 200, 300 is secured in the screw opening 110 and resists backing out of the screw opening 110 as will be discussed in detail hereinafter. At the same time, a distal end of screw assembly 200, 300 remains pivotable, while a proximal end of screw assembly 200, 300 is constrained within the cervical plate 100. Semi-constrained screw assemblies 200 and 300 will be discussed in detail further below.

Figure 1E:
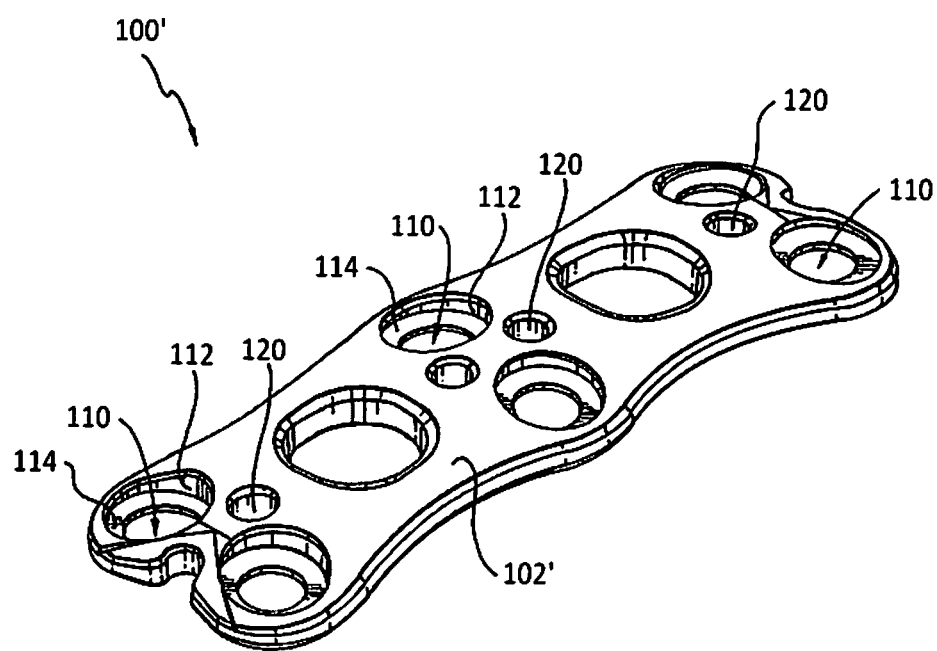
FIG. 1E is a perspective view of another embodiment of a cervical plate in accordance with the present disclosure.

Referring now to FIG. 1E, another embodiment of a cervical plate is shown, which is generally depicted as 100'. Essentially, cervical plate 100' has the same features of cervical plate 100, however, cervical plate 100' has a uniform body 102' that is configured in a one-piece configuration. Similarly to cervical plate 100, cervical plate 100' has a top surface and a bottom surface defining the thickness of the cervical plate 100'. In addition, cervical plate 100' includes a plurality of screw openings 110 and one or more guide openings 120, wherein the screw openings 110 and one or more guide openings 120 extend through the thickness of body 102' of cervical plate 100'. The one or more guide openings 120 are positioned along the central longitudinal axis of the cervical plate 100'. Each of the screw openings 110 has an annular sidewall 112 extending downwards from the top surface of body 102'. A lip 114 is located in each screw opening 110 in proximity to the bottom surface of the cervical plate assembly 100'. Similarly to cervical plate 100, lip 114 of cervical plate 100' is configured for engaging a semi-constrained screw 200, 300 (FIGS. 2A and 3A) such that rotating the screw 200, 300 causes the threads of an independent locking head 212, 312 of the respective screw 200, 300 to engage the lip 114.

Referring now to FIGS. 2A-2E, the semi-constrained screw assembly 200 according to the present disclosure will now be discussed. Screw assembly 200 is configured for use with both cervical plates 100 and 100', as discussed above. Screw assembly 200 includes an elongated shank 202, which is mechanically coupled to a removable tapered locking screw head 212. Shank 202 includes a neck portion 208 having an external flange 206 disposed at a proximal end 204 of shank 202 and a pointed tip portion 222 at a distal end 223 of the shank 202. The shank 202 has a uniform outer diameter and a first continuous helical thread 210 formed thereon for threaded insertion into bone. A second continuous helical thread 224 is formed on the independent head portion 212 for engaging lips 114 of screw plate 100. The pitch of the first thread 210 is greater than the pitch of the second thread 224. Each of the first and second threads 210, 224 has a substantially uniform pitch.

Referring now to FIGS. 2B-2E, removable head portion 212 includes one or more threaded segments 218 which have one or more slits 220 therebetween. The slits 220 run longitudinally through second threads 224 of threaded segments 218 and extend proximally from a distal end of head portion 212. Each threaded segment 218 also includes an inner flange 240 on an inner cavity 215 of head portion 212 to enable securement of the proximal end 204 of shank 202 with the head portion 212.

Figure 2A:
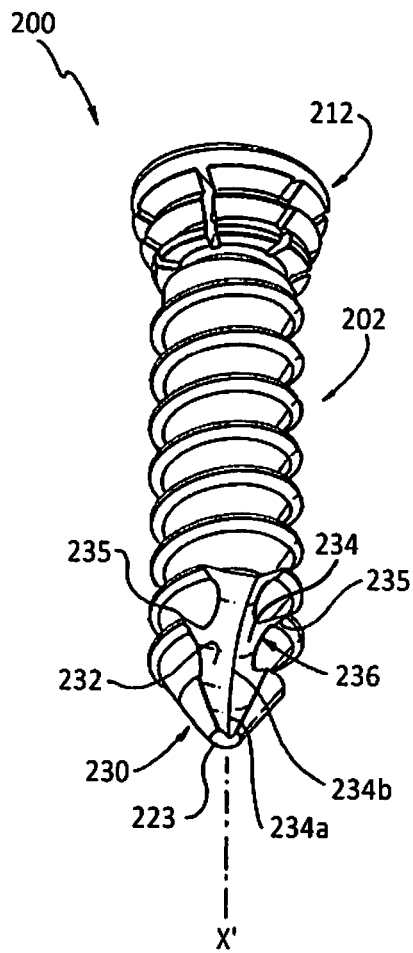
FIG. 2A is a perspective view of the semi-constrained screw assembly shown in FIG. 1A.
Figure 2B:
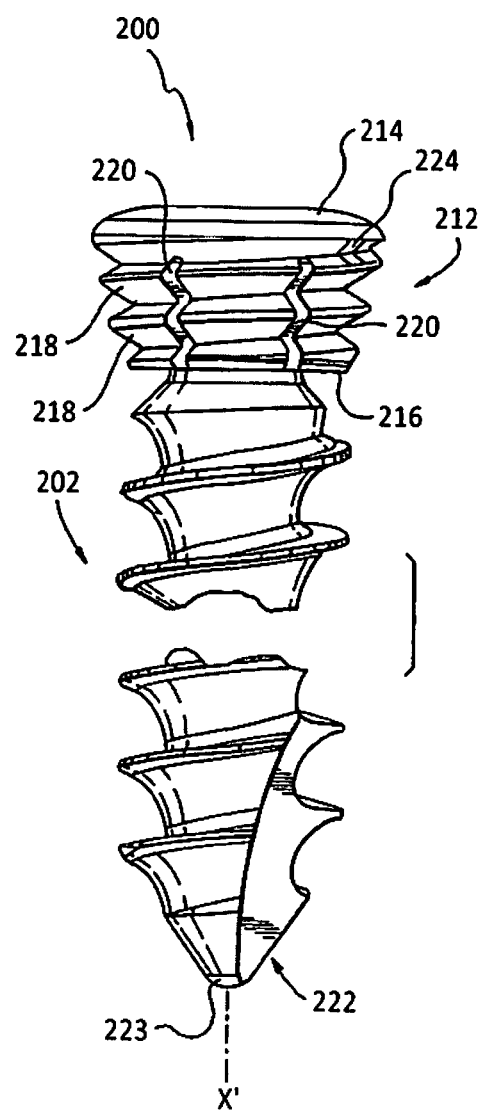
FIG. 2B is a side elevational view of the semi-constrained screw assembly of FIG. 2A.
Figure 2C:
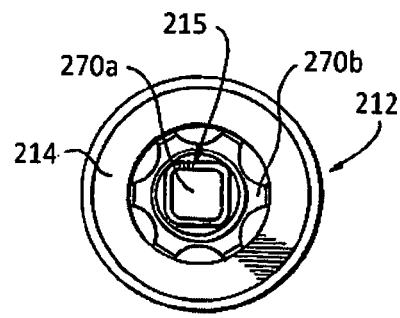
FIG. 2C is a top plan view of the semi-constrained screw assembly of FIG. 2A.
Figure 2E:
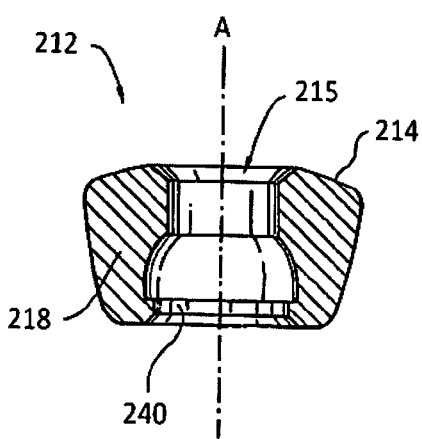
FIG. 2E is a side cross-sectional view of a removable screw head of the semi-constrained screw assembly of FIG. 2A.
Figure 2D:
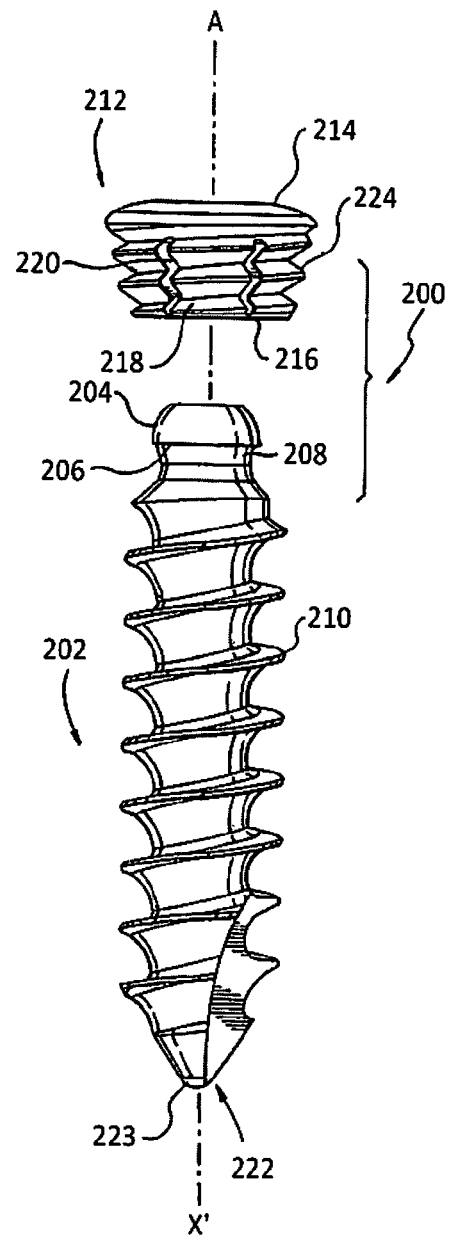
FIG. 2D is an exploded side view of the semi-constrained screw assembly of FIG. 2A.

In use, the distal end of removable head portion 212 is mechanically coupled onto the proximal end 204 of shank 202, whereby slits 220 operate to allow threaded segments 218 to expand outwardly at the distal end of head portion 212. Subsequently, the threaded segments 218 contract inwardly, to mechanically couple head portion 212 to the proximal end 204 of shank 202. More specifically, inner flanges 240 of tapered head portion 212 cam on the rounded proximal end of shank 202 until inner flanges 240 reach external flange portion 206 of shank 202 such that inner flanges 240 mechanically lock and seat onto neck portion 208. The independent head portion 212 configuration allows poly-axial movement of the shank 202 relative to the independent head portion 212 when the shank 202 and head portion 212 are mechanically coupled, as shown in FIG. 2B. As shown in FIGS. 2D and 2E, head portion 212 has a central longitudinal axis A. When semi-constrained screw assembly 200 is assembled, the shank 202 is pivotable and rotatable relative to the longitudinal axis A. In particular, the longitudinal axis X' of the shank 202 is pivotable with respect to the longitudinal axis A of the head portion 212 such that an acute angle may be defined therebetween. As shown in FIG. 2D, the longitudinal axis X' of the shank 202 is coaxially aligned with the longitudinal axis A of the head portion 212.

Bone screw 200 further includes a distal portion 230 that extends proximally from the pointed tip portion 222. In one embodiment, distal portion 230 may be configured such that bone screw 200 is a "self-starting" or "self drilling" bone screw. In other embodiments, distal portion 230 may be configured such that bone screw 200 is a "self-tapping" bone screw. In either embodiment, distal portion 230 includes first and second sidewalls 232, 234 that define a flute section 236. As shown in FIG. 2A by way of example, the first and second sidewalls 232, 234 of the flute section 236 extend from the pointed tip portion 222 to a crest 235 of thread 210 near the distal end of shank 202. The first sidewall 232 is planar and is aligned along a central longitudinal axis X' of the bone screw 200 such that first sidewall 232 is coplanar with the central longitudinal axis X'. As shown in FIG. 2A by way of example, the second sidewall 234 further includes a planar portion 234a that is parallel to the central longitudinal axis X' and an arcuate portion 234b that extends proximally from the planar portion 234a. The arcuate portion 234b is cut along a radius of curvature, as shown in FIG. 2A. Preferably, semi-constrained bone screws 200 are constructed of a material which is harder than the material of the lips 114 of cervical plates 100 and 100'. For example, the bone screw 200 may be made of titanium alloy (e.g., Ti-6Al-4V) with the lips 114 of cervical plates 100 and 100' made of a softer compatible material, such as a softer titanium material.

In use, screw 200 is driven through the screw opening in cervical plates 100 and 100' and into the bone. A screwdriver (not shown) having a square tip section and a hex shaped section slightly behind the square tip may be used to drive the semi-constrained screw 200 into cervical plates 100 and 100' and into the bone. The square tip of the screwdriver seats in square recess 270a of the proximal end 204 of the screw shank 202 (as shown in FIG. 2C). The hex shaped section of the screwdriver square tip seats in the hex-shaped opening 270b of the removable screw head 212 (as shown in FIG. 2C). In this manner, the screwdriver simultaneously drives both the screw shank 202 and the removable screw head 212. The screw shank 202 is driven into bone underlying cervical plates 100 and 100' until the second threads 224 on the screw head 212 engage the lip 114 of cervical plates 100 and 100' within the screw opening 110 of cervical plates 100 and 100'. It is envisioned that, the proximal end 214 of the screw head 212 is flush with the top side of cervical plates 100 and 100'. In this arrangement, bone screw 200 is advanced (i.e., rotated in a clock-wise direction) through any one of screw openings 110 of cervical plates 100 and 100' such that distal portion 230 of shank 202 engages vertebral bone for threadingly advancing thread 210 of shank 202 therein. Since the titanium of lips 114 is softer than the titanium alloy of the bone screw 200, as bone screw 200 is advanced through screw opening 110, threads 224 of threaded segments 218 engage the corresponding lip 110 to deform the lip 114 and secure bone screw assembly 200 in the corresponding screw opening 110 such that bone screw assembly 200 resists backing out of the screw opening 110. Further, head portion 212 of bone screw 200 is dimensioned to engage lips 110 to prevent further advancement of bone screw 200 toward vertebral bone. This type of screw locking arrangement is disclosed and shown in U.S. Pat. No. 6,322,562 to Wolter, the entire contents of which are hereby incorporated by reference herein.

As threads 220 of the screw head 212 engage the lip 114, screw shank 202 varies in angular orientations with respect to the axis of the screw opening 110. As screw shank 202 is driven into bone and the screw head 212 locked to cervical plates 100 and 100', the screw shank 202 remains free to articulate relative to the screw head 212 and, hence, the cervical plates 100 and 100'.

Figure 3A:
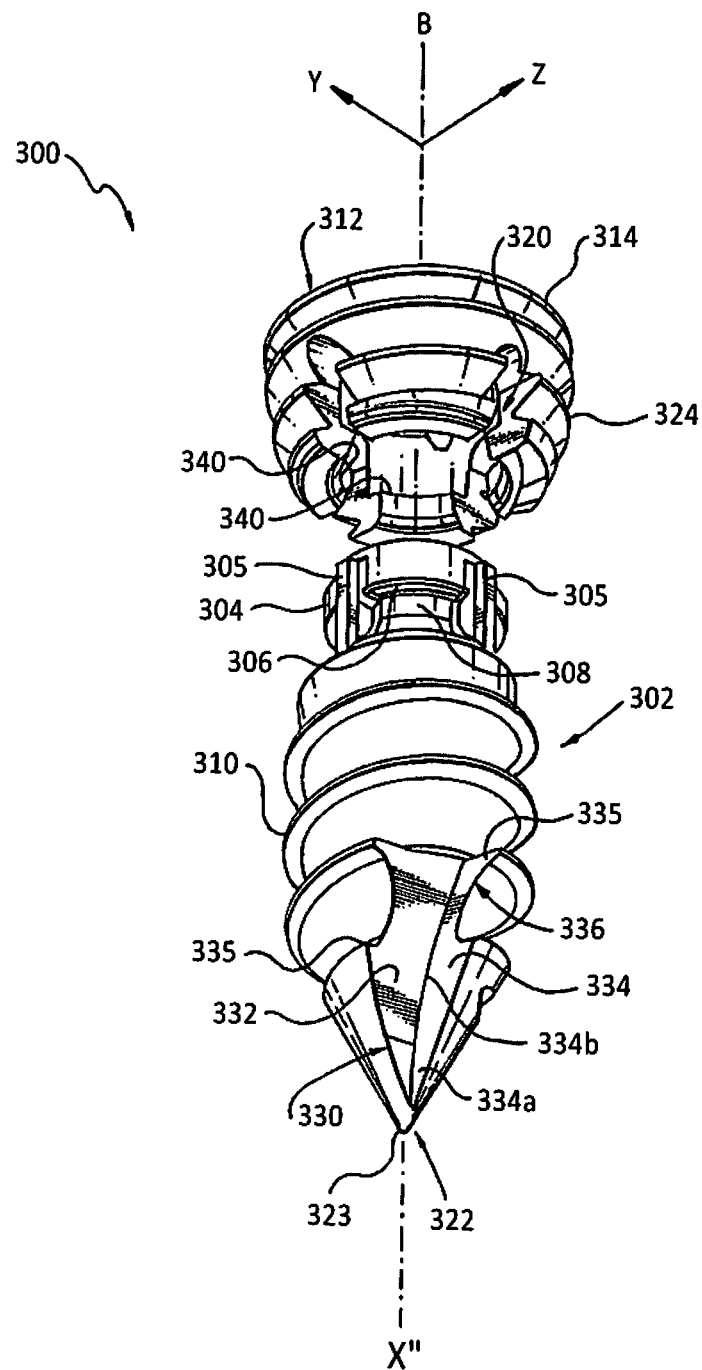
FIG. 3A is a perspective view of another embodiment of a semi-constrained screw assembly for use with the cervical plate system of FIG. 1A according to an embodiment of the present disclosure.
Figure 3B:
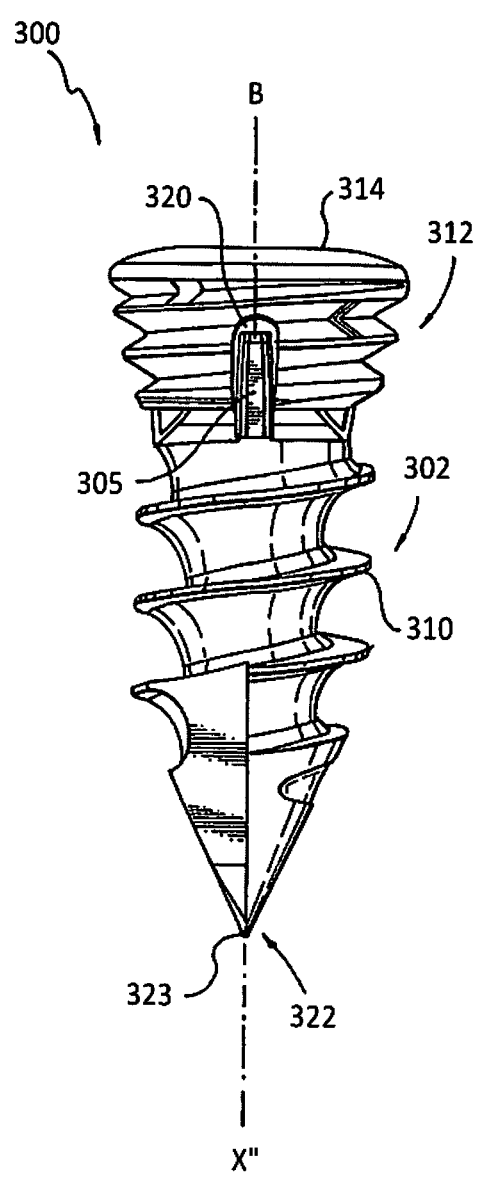
FIG. 3B is a side elevational view of the semi-constrained screw assembly of FIG. 3A.
Figure 3C:
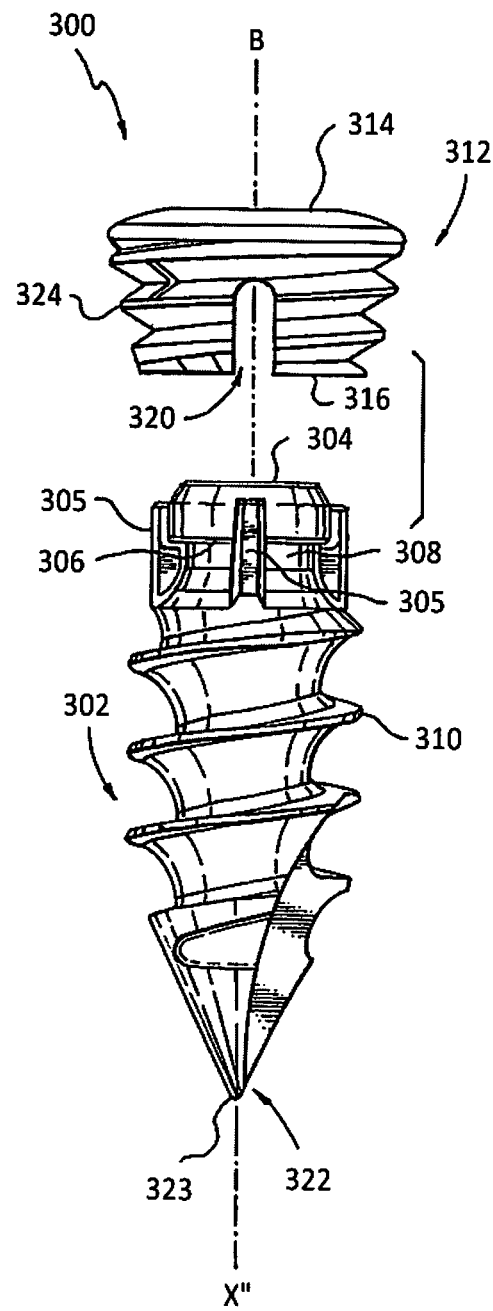
FIG. 3C is an exploded side view of the semi-constrained screw assembly of FIG. 3A.

Referring now to FIGS. 3A-3C, the semi-constrained screw assembly 300 according to the present disclosure will now be discussed. As described above with reference to bone screw 200, bone screw 300 is configured for use both with cervical plates 100 and 100' in the same manner as described hereinabove. Bone screw 300 includes a shank 302, a neck portion 308 extending between the shank 302 and a flange portion 306 disposed at a proximal end 304 of neck portion 308, an independent tapered head portion 312, and a pointed tip portion 322 at a distal end 323 of the shank 302. The shank 302 has a uniform outer diameter and a first continuous helical thread 310 formed thereon for threaded insertion into bone. A second continuous helical thread 323 is formed on the independent head portion for engaging lips 114 of cervical plates 100 and 100'. The pitch of the first thread 310 is greater than the pitch of the second thread 324. Each of the first and second threads 310, 324a has a substantially uniform pitch.

Removable head portion 312 includes one or more threaded segments 318, which have one or more slots 320 therebetween. The slots 320 run longitudinally through second threads 324 of threaded segments 318 and extend proximally from a distal end of head portion 312. Each threaded segment 318 also includes an inner flange 340 on an inner cavity 315 of head portion 312 to enable securement of the proximal end 304 of shank 302.

In use, the distal end of removable head portion 312 is mechanically coupled onto the proximal end 304 of shank 302, whereby slots 320 operate to allow threaded segments 318 to expand outwardly at the distal end of head portion 312. Subsequently, the threaded segments contract inwardly, to mechanically couple head portion 312 to the proximal end 304 of shank 302. More specifically, inner flanges 340 of tapered head portion 312 cam on the rounded proximal end of shank 302 until inner flanges 340 reach external flange portion 306 of shank 302 such that inner flanges 340 mechanically lock into neck portion 308.

A plurality of splines 305 are disposed along neck portion 308 and generally extend between a proximal end of first thread 310 and the longitudinal thickness of flange portion 306 and proximal end 304. Each slot 320 is configured to align with and receive a corresponding spline 305 to facilitate the mechanical coupling of head portion 312 to the proximal end 304 of shank 302. The independent head portion 312 configuration allows bi-axial movement (e.g., Y-Z axis shown in FIG. 3A) of the shank 302 relative to the independent head portion 312 when the shank 302 and head portion 312 are mechanically coupled, as shown in FIG. 3B. In this manner, shank 302 is configured to move in an axial motion only where splines 305 engage with the corresponding slots 320, thus limiting movement only in a Y direction and a Z direction. Thus, the shank 302 has a predetermined amount of pivotable movement relative to a longitudinal axis B of head portion 312 and is inhibited from rotating about longitudinal axis B in contrast to semi-constrained screw assembly 200. To facilitate expanding of the distal end 316 of head portion 312, one or more slits (not shown) may be defined longitudinally through second thread 324 (i.e., parallel to slots 320). As head portion 312 is engaged by a screw driver (not shown) to cause rotation of bone screw 300 in a clock-wise and/or counter clock-wise direction, the slots 320 defined through second thread 324 lockably engage corresponding splines 305 disposed along neck portion 308 to cause shank 302 to correspondingly rotate with head portion 312.

Bone screw 300 further includes a distal portion 330 that extends proximally from the pointed tip portion 322. In one embodiment, distal portion 330 may be configured such that bone screw 300 is a "self-starting" or "self drilling" bone screw. In other embodiments, distal portion 330 may be configured such that bone screw 300 is a "self-tapping" bone screw. In either embodiment, distal portion 330 includes first and second sidewalls 332, 334 that define a flute section 336. As shown in FIG. 3B by way of example, the first and second sidewalls 332, 334 of the flute section 336 extend from the pointed tip portion 322 to a crest 335 of thread 310 near the distal end of shank 302. The first sidewall 332 is planar and is aligned along a central longitudinal axis X" of the bone screw 300 such that first sidewall 332 is coplanar with the central longitudinal axis X". As shown in FIG. 3A by way of example, the second sidewall 334 further includes a planar portion 334a that is parallel to the central longitudinal axis X" and an arcuate portion 334b that extends proximally from the planar portion 334a. The arcuate portion 334b is cut along a radius of curvature, as shown in FIG. 3A. Bone screws 300 are constructed of a material which is harder than the material of the lips 114 of cervical plates 100 and 100'. For example, the bone screw assembly 300 may be made of titanium alloy (e.g., Ti-6Al-4V) with the lips 114 of cervical plates 100 and 100' made of a softer compatible material, such as a softer titanium material. Similarly to bone screw assembly 200, as described above, bone screw assembly 300 is configured to lock into the lip 114 of cervical plates 100 and 100'. Thus, semi-constrained screw assembly 300 is prevented from backing out during normal use.

What is claimed is:

1. A bone plate assembly comprising:
   a bone plate including an upper surface and a lower surface opposite the upper surface, the lower surface adapted to contact bone, the bone plate having at least one opening extending therethrough, the at least one opening including an annular non-threaded sidewall and a non-threaded lip adjacent the lower surface of the bone plate, the lip extending inwardly from the sidewall and defining a planar surface extending from the sidewall towards a center of the opening; and
   at least one bone screw including a shank and a head, the shank being repositionable with respect to the head when the head is secured in the at least one opening in the bone plate, the lip configured for engagement with the head when the head is secured in the at least one opening;
   wherein the shank includes a uniform outer diameter and a first continuous helical thread adapted to engage bone and the head includes a tapered configuration and a second continuous helical thread for coupling with the lip of the at least one opening of the bone plate, wherein the head of the at least one bone screw is constructed of a material which is harder than a material of the lip of the at least one opening in the bone plate.

2. The bone plate assembly according to claim 1, wherein the head of the at least one bone screw is releasably coupled to the shank.

3. The bone plate assembly according to claim 1, wherein the head includes a plurality of threaded segments that define at least one slot therebetween and the at least one slot runs longitudinally along the head and extends proximally from a distal portion of the head.

4. The bone plate assembly according to claim 3, wherein the distal portion of the head is mechanically coupled onto a proximal portion of the shank, whereby the at least one slot operably allows the plurality of threaded segments to expand outwardly at the distal portion of the head.

5. The bone plate assembly according to claim 3, wherein the shank further includes at least one spline disposed on a neck of the shank.

6. The bone plate assembly according to claim 5, wherein the at least one slot is configured to align with and receive the corresponding at least one spline to facilitate mechanical coupling of the head to a proximal portion of the shank.

7. The bone plate assembly according to claim 1, wherein the sidewall is annular between the lip and a top surface of the bone plate.

8. The bone plate assembly according to claim 1, wherein the head of the bone screw deforms the lip of the at least one opening and couples the bone screw to the bone plate.

9. The bone plate assembly according to claim 1, wherein the at least one opening has a first diameter at the upper surface and a second diameter at the lower surface, the first diameter being greater than the second diameter.

10. A bone plate assembly comprising:
    a bone plate including an upper surface and a lower surface opposite the upper surface, the lower surface adapted to contact bone, the bone plate having at least one opening extending therethrough, the at least one opening including an annular non-threaded sidewall and a non-threaded lip adjacent the lower surface of the bone plate, the lip extending inwardly from the sidewall and defining a planar surface extending from the sidewall towards a center of the opening; and
    at least one bone screw including a shank and a head, the shank being repositionable with respect to the head when the head is secured in the at least one opening in the bone plate, the lip configured for engagement with the head when the head is secured in the at least one opening;
    wherein the shank includes a uniform outer diameter and a first continuous helical thread adapted to engage bone and the head includes a tapered configuration and a second continuous helical thread for coupling with the lip of the at least one opening of the bone plate, wherein the head includes a plurality of threaded segments that define at least one slot therebetween and the at least one slot runs longitudinally along the head and extends proximally from a distal portion of the head, wherein the shank further includes at least one spline disposed on a neck of the shank, wherein the at least one spline and the corresponding at least one slot allow bi-axial movement of the shank relative to the head when the shank and the head are mechanically coupled, thereby allowing the shank to move in an axial motion only where the at least one slot engages the corresponding at least one spline, thus limiting movement to a first direction and a second direction.

11. A bone plate assembly comprising:
    a bone plate including an upper surface and a lower surface opposite the upper surface, the lower surface adapted to contact bone, the bone plate having at least one opening extending therethrough, the at least one opening including an annular non-threaded sidewall and a non-threaded lip adjacent the lower surface of the bone plate, the lip extending inwardly from the sidewall and defining a planar surface extending from the sidewall towards a center of the opening; and
    at least one bone screw including a shank and a head, the shank being repositionable with respect to the head when the head is secured in the at least one opening in the bone plate, the lip configured for engagement with the head when the head is secured in the at least one opening; wherein the shank includes a uniform outer diameter and a first continuous helical thread adapted to engage bone and the head includes a tapered configuration and a second continuous helical thread for coupling with the lip of the at least one opening of the bone plate, wherein the bone plate includes a plurality of sections moveable relative to one another, each section including at least one of the openings of the bone plate therethrough.

12. The bone plate assembly according to claim 11, wherein the bone plate is transitionable between a first expanded state where adjacent sections define a gap therebetween and a second collapsed state where the gap is reduced.

13. The bone plate assembly according to claim 11, wherein each section defines at least one finger and at least one slot for receiving the at least one finger of an adjacent section.

* * * * *